(12) United States Patent
Nishimura et al.

(10) Patent No.: US 6,610,709 B1
(45) Date of Patent: Aug. 26, 2003

(54) 2-N-SUBSTITUTED OR UNSUBSTITUTED-2-AMINO-5-METHYLPIPERIDINE-3,4-DIOLS AND PROCESSES FOR THE PREPARATION THEREOF

(75) Inventors: Yoshio Nishimura, Komae (JP); Eiki Shitara, Yokohama (JP); Tomio Takeuchi, Tokyo (JP)

(73) Assignees: Zaidan Hojin Biseibutsu Kagaku Kenkyu Kai, Tokyo (JP); Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/890,462
(22) PCT Filed: Feb. 2, 2000
(86) PCT No.: PCT/JP00/00572

§ 371 (c)(1),
(2), (4) Date: Aug. 1, 2001

(87) PCT Pub. No.: WO00/46200

PCT Pub. Date: Oct. 8, 2000

(30) Foreign Application Priority Data

Feb. 2, 1999 (JP) ............................................ 11-025175

(51) Int. Cl.$^7$ ...................... A61K 31/445; C07D 401/04
(52) U.S. Cl. ...................... 514/329; 514/323; 514/328; 546/200; 546/242; 546/244
(58) Field of Search ................. 514/323, 328, 514/329; 546/200, 242, 244

(56) References Cited

U.S. PATENT DOCUMENTS 5,013,842 A * 5/1991 Fleet et al. ................ 546/220
5,342,951 A * 8/1994 Koszyk et al. ............. 546/217

FOREIGN PATENT DOCUMENTS

EP 0481950 * 4/1992

* cited by examiner

Primary Examiner—Ceila Chang
(74) Attorney, Agent, or Firm—Larson & Taylor PLC

(57) ABSTRACT

This invention relates to (2R,3S,4R,5R)-2-amino-5-methylpiperidine-3,4-diol or a (2S,3S,4R,5R)-2-N-substituted-2-amino-5-methylpiperidine-3,4-diol represented by the general formula (I):

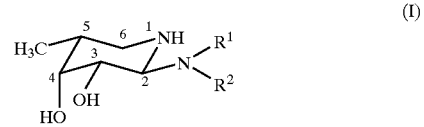

wherein $R^1$ and $R^2$ each are a hydrogen atom, or $R^1$ is a hydrogen atom and $R^2$ is a lower alkanoyl group or a lower ω-trihaloalkanoyl group, or $R^1$ and $R^2$ together denote phthaloyl group, and a pharmaceutically acceptable salt thereof. Said compound can be prepared from a (2S,3S,4R)-5-N-protected-2,3,4-O-tri-protected-5-aminopentane-1,2,3,4-tetraol by multi-steps of reactions.

13 Claims, No Drawings

2-N-SUBSTITUTED OR UNSUBSTITUTED-2-AMINO-5-METHYLPIPERIDINE-3,4-DIOLS AND PROCESSES FOR THE PREPARATION THEREOF

This application is a 371 application of PCT/JP00/00572 filed Feb. 2, 2000.

TECHNICAL FIELD

This invention relates to a 2-N-substituted or unsubstituted-2-amino-5-methylpiperidine-3,4-diol which is a novel compound having an inhibitory activity against glycosidases, or pharmaceutically acceptable salts thereof. This invention also relates to a process for the preparation of such a novel compound. Furthermore, this invention relates to a novel glycosidase inhibitor consisting of such a novel compound. Moreover, this invention relates to a pharmaceutical composition comprising as an active ingredient said 2-N-substituted or unsubstituted-2-amino-5-methylpiperidine-3,4-diol having an inhibitory activity against glycosidases. Besides, this invention includes an intermediate compound to be used for the synthesis of said novel compound.

BACKGROUND ART

Various glycosidases which are a glycoside hydrolase are an enzyme which is distributed widely in animal cells, microorganisms, viruses, and so on. In mammalian animals, it has been considered that glycosidases control a great variety of physiological mechanisms, including oncogenesis, metastasis of cancer cells, viral or bacterial infection, inflammation, immunological functions, fertilization of an ovum, and others, in which carbohydrate chains of glycoproteins and glycolipids can participate through the carbohydrate metabolism. Moreover, certain glycosidases participate in the digestive mechanism of food through the degradation of polysaccharides such as starch and sucrose, and oligosaccharides. Furthermore, it has been found that such a substance, which is inhibitory to glycosidases capable of liberating the carbohydrate chains bound to the surface of a cell membrane, is possible to have an immunomodulating action, an action of controlling inflammation and an action of controlling the metastasis of cancer cells, as well as an action of controlling infection of an AIDS virus or an influenza virus. Moreover, such substances that are inhibitory to glycosidases having catabolism which can participate in the digestive mechanism of food are found to be important, since they are useful as an antidiabetic agent or an agent for obesity.

Thus, in view that glycosidases are an enzyme which is important in the living body, it is also important to study physiological properties of glycosidases. In the study of the properties of glycosidases, use can be made of a substance having an action which inhibits the enzymatic activities of glycosidases. Moreover, it can be expected that certain glycosidase-inhibitory substances can be utilized as an inhibitor to the metastasis of cancer cells, and chronic articular rheumatism.

Therefore, it has been keenly demanded to provide such a novel compound which is of low toxicity, which is water-soluble and which has a potent inhibitory activity against glycosidases.

DISCLOURE OR INVENTION

It is an object of this invention to provide a novel compound having a potent inhibitory activity against glycosidases, and also to provide a novel glycosidase inhibitor. Moreover, it is another object of this invention to provide a process for the preparation of such a novel compound.

In order to achieve the above-mentioned objects of this invention, we, the present inventors, have paid attention to 1-N-iminosugars which are active as a glycosidase inhibitor, and we eagerly have made research about these 1-N-iminosugars. As a result, the present inventors have now succeeded in synthesizing several novel piperidine derivatives which have a potent inhibitory activity against glycosidases and which are represented by the general formula (I) given hereinafter. Moreover, the present inventors have now found a new preparation process which is able to synthesize efficiently the novel piperidine derivatives of the general formula (I). Based on these findings, the present inventors have completed this invention.

According to the first aspect of this invention, therefore, there is provided (2R,3S,4R,5R)-2-amino-5-methypiperidine-3,4-diol or a (2S,3S,4R,5R)-2-N-substituted-2-amino-5-methylpiperidine-3,4-diol represented by the general formula (I):

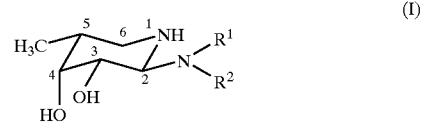

(I)

wherein $R^1$ and $R^2$ each are a hydrogen atom, or $R^1$ is a hydrogen atom and $R^2$ is a lower alkanoyl group or a lower ω-trihaloalkanoyl group, or $R^1$ and $R^2$ together denote a phthaloyl group, or a pharmaceutically acceptable salt thereof.

The salt of the compound of the general formula (I), which is provided according to the first aspect of this invention, includes acid addition salts at the imino group of the compound of the general formula (I). Such acid addition salts include, in particular, such pharmaceutically acceptable acid addition salts of said compound with a pharmaceutically acceptable inorganic acid such as hydrochloric acid and sulfuric acid or a pharmaceutically acceptable organic acid such as acetic acid, propionic acid, and the like.

In the compound of the general formula (I), the lower alkanoyl group or lower ω-trihaloalkanoyl group mentioned for the definition of $R^2$ is preferably acetyl group, trifluoroacetyl group or trichloroacetyl group, but generally may be the known lower alkanoyl groups or lower ω-trihaloalkanoyl groups which are conventionally used in chemistry of an amino sugar.

Examples of the compound of the general formula (I), which is provided according to the first aspect of this invention, include such compounds given in the following (1) to (5):

(1) (2S,3S,4R,5R)-2-acetamido-5-methylpiperidine-3,4-diol represented by the formula (Ia):

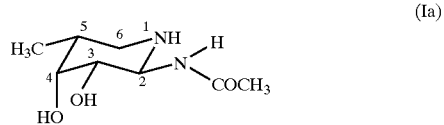

(Ia)

(2) (2S,3S,4R,5R)-2-trifluoroacetamido-5-methyl-piperidine-3,4-diol represented by the formula (Ib):

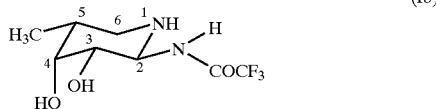

(3) (2S,3S,4R,5R)-2-trichloroacetamido-5-methyl-piperidine-3,4-diol represented by the formula (Ic):

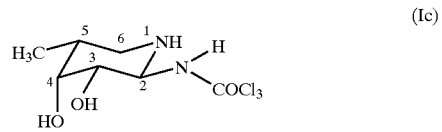

(4) (2S,3S,4R,5R)-2-phthalimido-5-methylpiperidine-3,4-diol represented by the formula (Id):

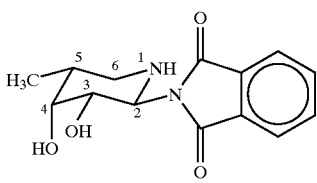

and (5) (2R,3S,4R,5R)-2-amino-5-methylpiperidine-3,4-diol represented by the formula (Ie):

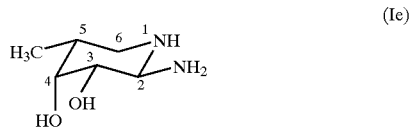

Next, there are described the physicochemical properties of (2S,3S,4R,5R)-2-acetamido-5-methylpiperidine-3,4-diol of the formula (Ia), (2S,3S,4R,5R)-2-trifluoro-acetamido-5-methylpiperidine-3,4-diol of the formula (Ib), (2S,3S,4R,5R)-2-trichloroacetamido-5-methylpiperidine-3,4-diol of the formula (Ic), (2S,3S,4R,5R)-2-phthalimido-5-methylpiperidine-3,4-diol of the formula (Id) and (2R,3S,4R,5R)-2-amino-5-methylpiperidine-3,4-diol of the formula (Ie), among the compound of the general formula (I) which are provided according to the first aspect of this invention.

1. Hydrochloride of (2S,3S,4R,5R)-2-Acetamido-5-methylpiperidine-3,4-diol [the Compound of the Formula (Ia)]

Color and Appearance: Colorless amorphous solid; Molecular formula: $C_8H_{16}N_2O_3 \cdot HCl$; Specific rotation: $[\alpha]^{27}_D -32.3°$ (c 0.41, methanol); $^1$H-NMR spectrum (CD$_3$OD, δ ppm): 1.05 (3H, d, J=6.8 Hz, —CH$_3$), 1.95–2.06 (1H, m, H-5), 2.05 (3H, s, —NHCO$\underline{CH_3}$), 2.92 (1H, dd, J=12.2 and 3.9 Hz, H-6eq), 3.05 (1H, br t, J=12.5 Hz, H-6ax), 3.72 (1H, dd, J=10.3 and 2.4 Hz, H-3), 3.84–3.87 (1H, m, H-4), 4.91 (1H, d, J=10.3 Hz, H-2); IR spectrum (KBr): 3325, 1660, 1460, 1400, 1140, 1060, 910 cm$^{-1}$; Mass spectrum (FAB-MS): m/z 189.2 (M+H)$^+$, 176.1, 154.1, 137.1, 120.1, 107, 89, 77.

2. Hydrochloride of (2S,3S,4R,5R)-2-Trifluoroacetamido-5-methylpiperidine-3,4-diol [the Compound of the Formula (Ib)]

Color and Appearance: Colorless amorphous solid; Molecular formula: $C_8H_{13}N_2O_3F_3 \cdot HCl$; Specific rotation: $[\alpha]^{28}_D -42.3°$ (c 0.46, methanol); $^1$H-NMR spectrum (CD$_3$OD, δ ppm): 1.06 (3H, d, J=6.8 Hz, —CH$_3$), 1.95–2.06 (1H, m, H-5), 2.97 (1H, dd, J=12.2 and 4.4 Hz, H-6eq), 3.09 (1H, br t, J=12 Hz, H-6ax), 3.84 (1H, dd, J=10.3 and 2.4 Hz, H-3), 3.87–3.90 (1H, m, H-4), 4.99 (1H, d, J=10.3 Hz, H-2) IR spectrum (KBr): 3440, 3250, 2950, 2780, 1730, 1555, 1400, 1260, 1220, 1180, 1100, 990, 900 cm$^{-1}$; Mass spectrum (FAB-MS): m/z 243.2 (M+H)$^+$, 154.1, 137.1, 120.1, 107.1, 89, 77.

3. Hydrochloride of (2S,3S,4R,5R)-2-Trichloroacetamido-5-methylpiperidine-3,4-diol [the Compound of the Formula (Ic)]

Color and Appearance: Colorless amorphous solid; Molecular formula: $C_8H_{13}N_2O_3Cl_3 \cdot HCl$; Specific rotation: $[\alpha]^{23}_D -37.8°$ (c 0.23, methanol); $^1$H-NMR spectrum (CD$_3$OD, δ ppm): 1.07 (3H, d, J=6.8 Hz, —CH$_3$), 1.96–2.02 (1H, m, H-5), 2.99 (1H, dd, J=12.2 and 4.4 Hz, H-6eq), 3.07 (1H, br t, J=12 Hz, H-6ax), 3.88–3.91 (1H, m, H-4), 3.94 (1H, dd, J=10.3 and 2.4 Hz, H-3), 4.97 (1H, d, J=10.3 Hz, H-2); Mass spectrum (FAB-MS): m/z 293 (M+H)$^+$, 291.08 (M)$^+$, 170.18, 154.09, 136.09, 130.13, 112.06, 107.04, 89.03, 77.04.

4. Hydrochloride of (2S,3S,4R,5R)-2-Phthalimido-5-methylpiperidine-3,4-diol [the Compound of the Formula (Id)]

Color and Appearance: Colorless amorphous solid; Molecular formula: $C_{14}H_{16}N_2O_4 \cdot HCl$; Specific rotation: $[\alpha]^{23}_D -19.6°$ (c 0.25, methanol); $^1$H-NMR spectrum (CD$_3$OD, δ ppm): 1.11 (3H, d, J=6.8 Hz, —CH$_3$), 2.14–2.23 (1H, m, H-5), 3.10 (1H, dd, J=12.2 and 4.4 Hz, H-6eq), 3.23 (1H, br t, J=12 Hz, H-6ax), 3.99 (1H, br s, H-4), 4.54 (1H, dd, J=10.3 and 2.4 Hz, H-3), 5.44 (1H, d, J=10.3 Hz, H-2), 7.88–8.00 (4H, m, phthalimido); Mass spectrum (FAB-MS): m/z 277.19(M+H)$^+$, 265.17, 202.22, 170.17, 154.10, 136.09, 130.13, 107.04, 89.03, 77.04.

5. Hydrochloride of (2R,3S,4R,5R)-2-Amino-5-methyl-piperidine-3,4-diol [the Compound of the Formula (Ie)]

Color and Appearance: Colorless amorphous solid; Molecular formula: $C_6H_{14}N_2O_2 \cdot HCl$; Specific rotation: $[\alpha]^{27}_D -24.90$ (c 0.15, methanol); $^1$H-NMR spectrum (CD$_3$OD, δ ppm): 1.04 (3H, d, J=6.8 Hz, —CH$_3$), 1.95–2.02 (1H, m, H-5), 2.99–3.04 (2H, m, H-6), 3.55 (1H, dd, J=2.5 and 8.8 Hz, H-3), 3.84 (1H, br t, J=2.5 Hz, H-4), 4.42 (1H, d, J=8.8 Hz, H-2); $^{13}$C-NMR spectrum (CD$_3$OD, δ ppm): 14.21 (CH$_3$), 33.52 (C-5), 44.26 (C-6), 72.25 (C-3 or C-4), 72.99 (C-4 or C-3), 88.86 (C-2); Mass spectrum (FAB-MS): m/z 130.2 (M—NH$_3$+H)$^+$, 107.0, 89.0, 77.1.

The following Test Examples demonstrate that each of (2S,3S,4R,5R)-2-acetamido-5-methylpiperidine-3,4-diol of the formula (Ia), (2S,3S,4R,5R)-2-trifluoroacetamido-5-methylpiperidine-3,4-diol of the formula (Ib), (2S,3S,4R,5R)-2-trichloroacetamido-5-methylpiperidine-3,4-diol of the formula (Ic), (2S,3S,4R,5R)-2-phthalimido-5-methylpiperidine-3,4-diol of the formula (Id), and (2R,3S,4R,5R)-2-amino-5-methylpiperidine-3,4-diol of the formula (Ie) according to this invention has the glycosidase-inhibitory activity.

TEST EXAMPLE 1

This Test Example is a test example for determining the α-fucosidase-inhibitory activity of the compound of the general formula (I) according to this invention.

Assay of the α-fucosidase-inhibitory activity was conducted according to a modification of the method described in the "Journal of Biological Chemistry", 252, pp.5194–5200 (1977).

Thus, 0.5 mL of 0.025M citrate-phosphate buffer (pH 6.3), 0.1 mL of the same buffer containing 1.5 mM p-nitrophenyl α-L-fucopyranoside dissolved therein, and 0.1 mL of either water or an aqueous solution containing as the tested compound any one of the compounds of the formulae (Ia), (Ib), (Ic) and (Id) according to this invention were mixed with each other and pre-incubated in a 96-well titer plate at 37° C. for 10 minutes. After the completion of the pre-incubation, to the pre-incubated mixture was added 0.01 mL of 0.025M citrate-phosphate buffer containing α-L-fucosidase (a product of Sigma Company, originated from bovine liver) dissolved therein, and thereafter the enzymatic reaction was conducted at 37° C. for 60 minutes. After the enzymatic reaction, to the resulting reaction solution was added 1.0 mL of 0.2M glycine-sodium hydroxide buffer (pH 10.5), in order to terminate the enzymatic reaction. Thereafter, the absorbance (designated as "a") of light at 405 nm of the resulting reaction solution was measured. Concurrently, measurement was made of the absorbance (designated as "b") of light at 405 nm of the reaction solution as obtained in the control test where the enzymatic reaction was conducted without addition of the test compound. Further, measurements were made of the absorbance (designated as "a'") and the absorbance (designated as "b'") of light at 405 nm of the reaction solutions as obtained in the blank tests where the enzymatic reaction had not been conducted in the assay test, and also in the control test for the blank tests, respectively.

The rate of inhibition to α-L-fucosidase was calculated by the equation:

$$[1-(a-a')/(b-b')] \times 100.$$

The concentration of the test compound capable of exhibiting 50% inhibition to the enzyme was estimated as the value of $IC_{50}$. The test results obtained are summarized in Table 1 given hereinafter.

TEST EXAMPLE 2

This Test Example is a test example for determining the α-glucosidase or β-glucosidase-inhibitory activity of the compounds according to this invention.

The evaluation of the α- or β-glucosidase-inhibitory activity was conducted according to a modification of the method described in the "Agricultural and Biological Chemistry", 26, p.203 (1962). Namely, the test was conducted in the same manner as the test for the enzyme-inhibitory activity described in Test Example 1, except that either α-glucosidase originated from yeast, or β-glucosidase originated from almond (both enzymes are products of Sigma Company) was used as the glycosidase enzyme, and that p-nitrophenyl α-D-glucoside or p-nitrophenyl β-D-glucoside was used as the substrate. Furthermore, the enzyme-inhibitory activity was measured in the same manner as in Test Example 1, and the 50% inhibitions of the tested compounds against the enzymes were calculated, respectively. The results obtained are shown in Table 1 below.

TABLE 1

| Compound of the Invention | 50% Inhibiory Concentration ($IC_{50}$) (μg/ml) | | |
|---|---|---|---|
| | Enzyme A[a] | Enzyme B[b] | Enzyme C[c] |
| Compound of the Formula (Ia) | 0.11 | 40 | 2.3 |
| Compound of the Formula (Ib) | 0.003 | 5 | 55 |
| Compound of the Formula (Ic) | 0.003 | 5 | 50 |
| Compound of the Formula (Id) | 0.004 | 7 | 60 |
| Compound of the Formula (Ie) | 0.003 | 6 | 50 |

(Note)
[a]Enzyme A: α-L-fucosidase (from bovine liver)
[b]Enzyme B: α-D-glucosidase (from baker's yeast)
[c]Enzyme C: β-D-glucosidase (from almonds)

As shown in Table 1, the compound having the formula (Ia), (Ib), (Ic), (Id) or (Ie) according to the first invention is able to inhibit strongly α-L-fucosidase, α-D-glucosidase and β-D-glucosidase. Therefore, the compounds having the formulae (Ia), (Ib), (Ic), (Id) and (Ie) respectively according to this invention each are significantly effective as an inhibitor against said enzymes.

Moreover, it can be presumed that the compound having the formula (Ia), (Ib), (Ic), (Id) or (Ie) according to this invention has not only an activity to inhibit such glycosidases which participate in the mechanism of metastasis of cancer cells, the mechanism of inflammation and the mechanism of infection of an AIDS virus in mammalian animals, but also an activity to inhibit such glycosidases having a catabolism which participate in the digestive mechanism of food. In this view, the compound of this invention can be expected to be useful as an inhibitor to metastasis of cancer cells, which may be used for the therapeutic treatment of cancer; as an anti-inflammatory agent which may be used for treatment of chronic articular rheumatism; as an inhibitor to infection of an AIDS virus; and as an antidiabetic agent or an agent for obesity. Moreover, the compound of this invention is useful as a reagent for studying the functions of glycosidases in the living body.

Thus, according to the second aspect of this invention, there is provided a glycosidase inhibitor consisting of the compound represented by the general formula (I) or a salt thereof.

Next, there is described a process for the preparation of (2R,3S,4R,5R)-2-amino-5-methylpiperidine-3,4-diol and a (2S,3S,4R,5R)-2-N-substituted-2-amino-5-methylpiperidine-3,4-diol which are represented by the general formula (I).

In the preparation of such (2R,3S,4R,5R)-2-amino-5-methylpiperidine-3,4-diol or a (2S,3S,4R,5R)-2-N-substituted-2-amino-5-methylpiperidine-3,4-diol represented by the general formula (I) according to the first aspect of this invention, there is used as a first starting material, a (2S,3S,4R)-5-N-proteccted-2,3,4-O-tri-protected-5- aminoentane-1,2,3,4-tetraol represented by the general formula (II):

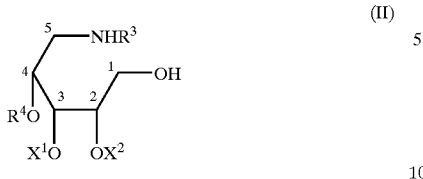

wherein $R^3$ is an amino-protecting group, $R^4$ is a hydroxyl-protecting group, and $X^1$ and $X^2$ each are a hydroxyl-protecting group, or $X^1$ and $X^2$ together denote one divalent hydroxyl-protecting group (which is an alkylidene group or an aralkylidene group) represented by the formula:

where $R^5$ and $R^6$ may be the same or different and each denote a hydrogen atom, an alkyl group or an aryl group, especially phenyl group, or $X^1$ and $X^2$ together denote a cycloalkylidene group or tetrahydropyranylidene group.

The compound of the general formula (II) may be prepared according to the method of Nishimura et al. as described in the "J. Am. Chem. Soc.", 110, p.7249–7250 (1988) and the "Bull. Chem. Soc. Jpn.", 65, p.978–986 (1996), as well as the method of Kudoh et al. as described in the "J. Antibiotics", 45, p.954–962 (1992).

The compound of the general formula (II) prepared according to the method as described above is employed as the starting compound and may be chemically converted in a plural of reaction steps, so that (2R,3S,4R,5R)-2-amino-5-methylpiperidine-3,4-diol and (2S,3S,4R,5R)-2-N-substituted-2-amino-5-methylpiperidine-3,4-diols of the general formula (I) can be prepared.

Therefore, according to the third aspect of this invention, there is provided a process for the preparation of (2R,3S,4R,5R)-2-amino-5-methylpiperidine-3,4-diol or a (2S,3S,4R,5R)-2-N-substituted-2-amino-5-methylpiperidine-3,4-diol represented by the general formula (I):

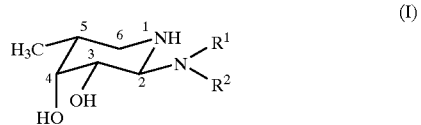

wherein $R^1$ and $R^2$ each are a hydrogen atom, or $R^1$ is a hydrogen atom and $R^2$ is a lower alkanoyl group or a lower ω-trihaloalkanoyl group, or $R^1$ and $R^2$ together denote phthaloyl group, characterized in that the process comprises:

eliminating the hydroxyl-protecting group ($R_4$) at the 4-position of a (2S,3S or 3R,4R)-5-N-protected-2,3,4-O-tri-protected-5-aminopentane-1,2,3,4-tetraol represented by the following general formula (II):

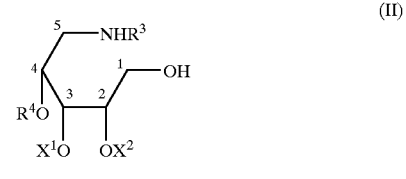

wherein $R^3$ is an amino-protecting group, $R^4$ is a hydroxyl-protecting group, and $X^1$ and $X^2$ each are a hydroxyl-protecting group, or $X^1$ and $X^2$ together denote one divalent hydroxyl-protecting group having the formula:

where $R^5$ and $R^6$ may be the same or different and each denote a hydrogen atom, an alkyl group or an aryl group, especially phenyl group, or $X^1$ and $X^2$ together denote a cycloalkylidene group or tetrapyranylidene group, to give a (2S,3R,4R)-5-N-protected-2,3-O-di-protected-5-aminopentane-1,2,3,4-tetraol represented by the general formula (III):

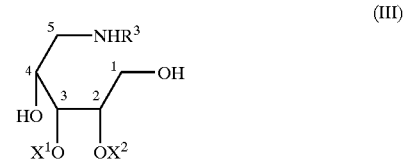

wherein $R^3$, $X^1$ and $X^2$ have the same meanings as above;
protecting the hydroxyl group at the 1-position of the compound of the general formula (III) with a hydroxyl-protecting group ($R^7$), to prepare a (2S,3R,4R)-5-N-protected-1,2,3-O-tri-protected-5-aminopentane-1,2,3,4-tetraol represented by the general formula (IV):

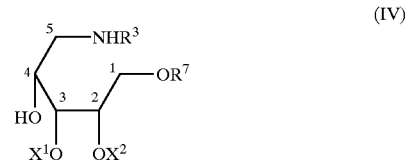

wherein R3, $X^1$ and $X^2$ have the same meanings as above and $R^7$ denotes a hydroxyl-protecting group;
oxidizing the hydroxyl group at the 4-position of the compound of the general formula (IV), to prepare a (2S,3S)-5-N-protected-1,2,3-O-tri-protected-4-keto-5-aminopentane-1,2,3-triol represented by the general formula (V):

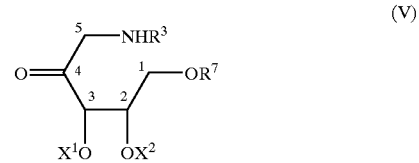

wherein $R^3$, $X^1$, $X^2$ and $R^7$ have the same meanings as above;

subjecting the oxo group at the 4-position of the compound of the general formula (V) to the Wittig reaction, so as to convert said oxo group into a methylene group, thereby producing a (2S,3S)-5-N-protected-1,2,3-O-tri-protected-4-methylene-5-aminopentane-1,2,3-triol represented by the general formula (VI):

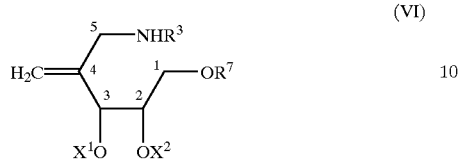

(VI)

wherein $R^3$, $R^7$, $X^1$ and $X^2$ have the same meanings as above;
eliminating the hydroxyl-protecting group ($R^7$) at the 1-position of the compound of the general formula (IV), to prepare a (2S,3S)-5-N-protected-2,3-O-di-protected-4-methylene-5-aminopentane-1,2,3-triol represented by the general formula (VII):

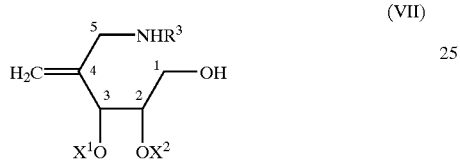

(VII)

wherein $R^3$, $X^1$ and $X^2$ have the same meanings as above;
oxidizing the hydroxyl group at the 1-position of the compound of the general formula (VII), with accompanying cyclization, to prepare a (2R,3R,4S)-1-N-protected-3,4-O-di-protected-5-methylenepiperidine-2,3,4-triol represented by the general formula (VIII):

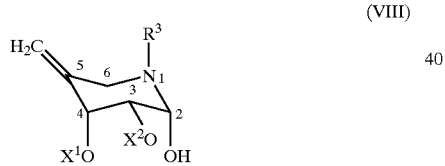

(VIII)

wherein $R^3$, $X^1$ and $X^2$ have the same meanings as above;
conducting the Mitsunobu reaction on the hydroxyl group at the 2-position of the compound of the general formula (VIII) by reaction with phthalimide, to prepare a (2S,3S,4S)-1-N-protected-3,4-O-di-protected-5-methylene-2-phthalimidopiperidine-3,4-diol represented by the general formula (IX):

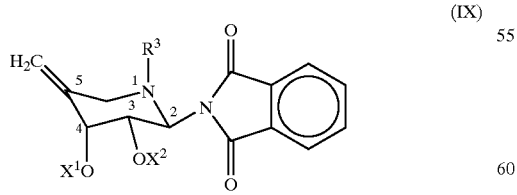

(IX)

wherein $R^3$, $X^1$ and $X^2$ have the same meanings as above;
reducing the double bond at the 5-position of the compound of the general formula (IX), to convert the methylene group into a methyl group, thereby preparing a (2S,3S,4R,5R)-1-N-protected-3,4-O-di-protected-5-methyl-2-phthalimidopiperidine-3,4-diol represented by the general formula (X):

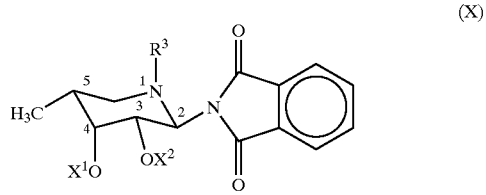

(X)

wherein $R^3$, $X^1$ and $X^2$ have the same meanings as above;
eliminating the phthaloyl group from the 2-amino group of the compound of the general formula (X) by treatment with hydrazine or an acid, to prepare a (2R,3S,4R,5R)-2-amino-1-N-protected-3,4-O-di-protected-5-methylpiperidine-3,4-diol represented by the general formula (XI):

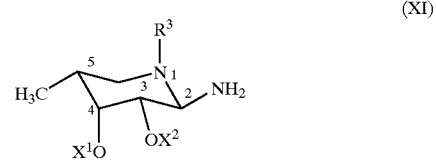

(XI)

wherein $R^3$, $X^1$ and $X^2$ have the same meanings as above;
protecting the amino group at the 2-position of the compound of the general formula (XI) with a lower alkanoyl group or a lower ω-trihaloalkanoyl group ($R^2$), to prepare a compound represented by the general formula (XII):

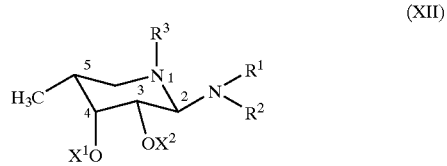

(XII)

wherein $R^3$, $X^1$ and $X^2$ have the same meanings as above, $R^1$ is a hydrogen atom and $R^2$ is a lower alkanoyl group or a lower ω-trihaloalkanoyl group; and then
eliminating both the imino-protecting group ($R^3$) and the hydroxyl-protecting groups ($X^1$ and $X^2$) of the compound of the general formula (XII), or alternatively eliminating the imino-protecting group(s) and the hydroxyl-protecting groups ($X^1$ and $X^2$) immediately from the compound of the general formula (X) or (XI), to give the compound of the formula (I).

In carrying out the process according to the third aspect of this invention, first of all, the (2S,3S,4R)-5-N-proteccted-2,3,4-O-tri-protected-5-aminopentane-1,2,3,4-tetraol of the general formula (II) is treated with an acid or a base in an organic solvent such as tetrahydrofuran and others. Alternatively, the compound of the general formula (II) where $R^4$ is an aralkyl group is reduced, or the compound of the general formula (II) where $R^4$ is silylether group is treated with a fluoride such as tertabutylammonium fluoride. Thereby, the hydroxyl-protecting group ($R^4$) at the 4-position of the compound of the general formula (II) is eliminated, to give the (2S,3R,4R)-5-N-proteccted-2,3-O-di-protected-5-aminopentane-1,2,3,4-tetraol of the general formula (III).

Then, the compound of the general formula (III) thus obtained is treated with a halogenated alkylsilane such as tert-butyl dimethylsilyl chloride and trimethylsilyl chloride, an alkoxyalkyl halide such as methoxyethoxymethyl chloride and methoxymethyl chloride, an alkyl halide, an aralkyl halide, an acid chloride such as acetyl chloride, or an acid anhydride such as acetic anhydride, in the presence of a base such as imidazole, diisopropylethylamine, triethylamine and pyridine, in a solvent such as N,N-dimethylformamide, methylene chloride, chloroform and tetrahydrofuran. Alternatively, the compound of the general formula (III) is treated with 2,3-dihydro-2H-pyran, 2,2-dimethoxypropane or others in the presence of an acid such as p-toluenesulfonic acid and others, in an organic solvent. Thereby, the hydroxyl group at the 1-position of the compound of the general formula (III) may be protected by a hydroxyl-protecting group ($R^7$), preferably tert-butyldimethylsilyl group, to give a (2S,3R,4R)-5-N-protected-1,2,3-O-tri-protected-5-aminopentane-1,2,3,4-tetraol of the general formula (IV).

Then, the compound the general formula (IV) thus obtained is treated with an oxidizing agent such as ruthenium tetraoxide, Dess-Martin Periodinane, manganese dioxide and a confirmation of oxalyl chloride with dimethyl sulfoxide, in a solvent such as methylene chloride, chloroform, carbon tetrachloride and tetrahydrofuran. Thereby, the hydroxyl group at the 4-position of the compound of the general formula (IV) may be oxidized, to give the (2S,3S)-5-N-protected-1,2,3-O-tri-protected-4-keto-5-aminopentane-1,2,3-triol of the general formula (V).

Subsequently, the compound of the general formula (V) so obtained is treated with methylenetriphenylphosphorane in a solvent such as tetrahydrofuran, methylene chloride, benzene, acetonitrile and N,N-dimethylformamide, to convert the oxo group at the 4-position thereof into the methylene group by the resulting wittig reaction. Thereby, the (2S,3S)-5-N-protected-1,2,3-O-tri-protected-4-methylene-5-aminopentane-1,2,3-triol of the general formula (VI) is prepared.

Thereafter, the compound of the general formula (VI) thus obtained is treated with an acid or a base in an organic solvent such as tetrahydrofuran and others. Alternatively, the compound of the general formula (VI) where $R^4$ is an aralkyl group may be reduced, or the compound of the general formula (VI) where $R^4$ is silylether group may be treated with a fluoride such as tertabutylammonium fluoride. Thereby, the hydroxyl-protecting group ($R^7$) at the 1-position of the compound of the general formula (VI) is eliminated, to give the (2S,3S)-5-N-proteccted-2,3-O-di-protected-4-methylenepentane-1,2,3-triol of the general formula (VII). Thereafter, the compound the general formula (VII) so obtained is treated with an oxidizing agent such as ruthenium tetraoxide, Dess-Martin Periodinane, manganese dioxide and a confirmation of oxalyl chloride with dimethyl sulfoxide, in a solvent such as methylene chloride, chloroform, carbon tetrachloride and tetrahydrofuran. Thereby, the hydroxyl group at the 1-position of the compound of the general formula (VII) may oxidized and the cyclization of the compound is accompanied, to give the (2R,3R,4S)-1-N-protected-3,4-O-di-protected-5-methylenepiperidine-2,3,4-triol of the general formula (VIII).

The 2-hydroxyl group of the compound of the general formula (VIII) thus obtained is then subjected to the Mitsunobu reaction by treatment with phthalimide in a solvent such as methylene chloride, tetrahydrofuran, chloroform, benzene, acetonitrile and N,N-dimethylformamide, to give the (2S,3S,4S)-1-N-protected-3,4-O-di-protected-5-methylene-2-phthalimidopiperidine-3,4-diol of the general formula (IX):

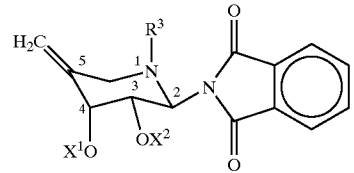

(IX)

wherein $R^3$, $X^1$ and $X^2$ have the same meanings as above.

Then, the double bond at the 5-position of the compound of the general formula (IX) so obtained is reduced in the presence of a catalyst such as palladium, platinum oxide and Raney nickel, to convert the methylene group at the 5-position thereof into methyl group, whereby the (2S,3S,4R, 5R)-1-N-protected-3,4-O-di-protected-5-methyl-2-phthalimidopiperidine-3,4-diol of the general formula (X) is prepared.

Subsequently, the compound of the formula (X) thus obtained is treated with hydrazine or an acid such as hydrochloric acid, in a solvent such as methanol, to eliminate the phthaloyl group, whereby the (2R,3S,4R,5R)-2-amino-1-N-protected-3,4-O-di-protected-5-methylpiperidine-3,4-diols represented by the general formula (XI):

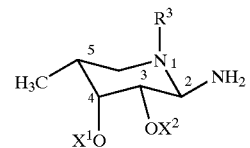

(XI)

wherein $R^3$, $X^1$ and $X^2$ have the same meanings as above, can be prepared.

Thereafter, the compound of the formula (XI) as obtained is treated with an agent for introducing a lower alkanoyl group or a lower ω-trihaloalkanoyl group, for example, an acid anhydride such as acetic anhydride and trifluoroacetic anhydride; an acid chloride such as acetyl chloride, trifluoroacetyl chloride and trichloroacetyl chloride; an alkyl halide such as a lower alkyl bromide, or an aryl halide such as benzyl bromide, in the presence of a base such as triethylamine, pyridine and diisopropylethylamine in a solvent such as methylene chloride, chloroform and tetrahydrofuran. By using these agents for introducing a lower alkanoyl group or a lower ω-trihaloalkanoyl group, the amino group at the 2-position of the compound of the formula (XI) may be protected by the lower alkanoyl group or the lower ω-trihaloalkanoyl group ($R^2$). Thereby, prepared is the compound represented by the general formula (XII):

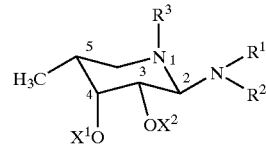

(XII)

wherein $R^3$, $X^1$ and $X^2$ have the same meanings as above, $R^1$ is a hydrogen atom and $R^2$ is a lower alkanoyl group or a lower ω-trihaloalkanoyl group.

Then, the compound of the general formula (XII) thus obtained is either treated with an acid such as hydrochloric acid or a base such as potassium carbonate, in a solvent such as methanol, methylene chloride, chloroform and tetrahydrofuran, or reduced in the presence of a catalyst such as palladium, platinum oxide and Raney nickel, depending on the sort of the protecting groups ($R^3$, $X^1$ and $X^2$), thereby to eliminate both of the imino-protecting group ($R^3$) and the hydroxyl-protecting groups ($X^1$ and $X^2$). Alternatively, immediately from the compound of the general formula (X) or (XI), both of the imino-protecting group and the hydroxyl-protecting groups ($X^1$ and $X^2$) may be eliminated by the same deprotection method as above. Thus, there can be produced said (2R,3S,4R,5R)-2-amino-5-methylpiperidine-3,4-diol or (2S,3S,4R,5R)-2-N-substituted-2-amino-5-methylpiperidine-3,4-diol of the general formula (I):

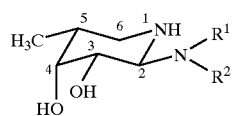

(I)

wherein $R^1$ and $R^2$ have the same meanings as above.

When the compound of the general formula (I) so prepared by the process according to the third aspect of this invention is obtained in the form of its acid addition salt such as hydrochloride, an aqueous solution of such acid addition salt may be treated with a cation-exchange resin, for example, Dow X 50W (a product of Dow Chemical Co., U.S.A)($H^+$ type) according to conventional procedures, or may be purified by a chromatography using a solvent system containing ammonia, to obtain the compounds of the formula (I) in the form of the free base.

Furthermore, as will be apparent from Test Examples 1 to 2 as described hereinbefore, each of the (2R,3S,4R,5R)-2-amino-5-methylpiperidine-3,4-diol or (2S,3S,4R,5R)-2-N-substituted-2-amino-5-methylpiperidine-3,4-diol of the general formula (I), which each are a novel compound according to this invention, has the glycosidase-inhibitory activity. Therefore, all of these novel piperidine derivatives, owing to its glycosidase-inhibitory activity, is useful as an inhibitor to the metastasis of cancer cells and also is useful for the therapeutic treatment or prevention of diabetes and obesity. Furthermore, the novel piperidine derivatives according to this invention may be admixed with a conventional and pharmaceutically acceptable solid or liquid carrier to be formulated into a pharmaceutical composition.

According to the fourth aspect of this invention, therefore, there is provided a pharmaceutical composition comprising as an active ingredient (2R,3S,4R,5R)-2-amino-5-methylpiperidine-3,4-diol or a (2S,3S,4R,5R)-2-N-substituted-2-amino-5-methylpiperidine-3,4-diol of the general formula (I), or a pharmaceutically acceptable salt thereof, in combination with a pharmaceutically acceptable carrier.

The pharmaceutical composition according to the fourth aspect of this invention has a glycosidase-inhibitory activity and may be administered as a medicine to animals, including human. Particularly, the pharmaceutical composition according to the fourth aspect of this invention is effective in the therapeutic treatment of cancers, or the therapeutic treatment and prevention of diabetes or obesity.

In the pharmaceutical composition according to the fourth aspect of this invention, the carrier to be mixed may be a solid or liquid carrier which is used conventionally in pharmaceutical techniques. The solid carrier may be, for example, starch, lactose, crystalline cellulose or calcium carbonate, and the liquid carrier may be, for example, physiological saline, aqueous ethanol or ethanol. The proportion of the novel piperidine derivative contained as an active ingredient in the composition is not limited, as far as it is sufficient to treat diseases, but it may be, for example, in a range of from not less than 0.01% to less than 100%, preferably in a range of from not less than 0.1% to less than 80%, based on the total weight of the composition.

When the pharmaceutical composition according to the fourth aspect of this invention is administered to the patients, it may be formulated according to conventional procedures, depending on various sorts of carriers used, the mode of administration or the medicinal form used. The formulations for oral administration include tablets, pills, granules, capsules, powders, liquids, suspensions, syrups, sublingual medicine, etc. Moreover, the formulations for parenteral administration include injections, percutaneous absorbents, inhalations, suppositories, and others. In the formulation, additives for medicines, such as surface active agents, excipients, stabilizers, wetting agents, disintegrating agents, dissolution auxiliary agents, isotonic agents, buffer agents, colorants and flavors may suitably be incorporated.

The optimal dosage of the novel piperidine derivative of this invention to be used as a medicine may vary depending on age and body weight of the patients, the type and conditions of disorders to be treated, and the route of administration employed. However, when orally administered to human, the dosage may be in a range of 1.0 to 1000 mg/kg per day for one adult. When intravenously administered, the piperidine derivative may similarly be administered in a range of 1.0 to 100 mg/kg.

Furthermore, the compound of the general formula (IX), which is prepared as an intermediate in a step of the preparation process according to the third aspect of this invention, is a novel compound and is useful for the preparation of the compound of the general formula (I) according to the first aspect of this invention. According to the fifth aspect of this invention, therefore, there is provided a (2S,3S,4S)-1-N-protected-3,4-O-di-protected-5-methylene-2-phthalimido-piperidine-3,4-diol represented by the general formula (IX):

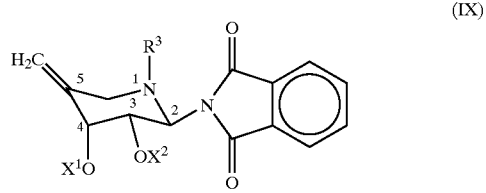

(IX)

wherein $R^3$ is an imino-protecting group, especially tert-butoxycarbonyl group, and $X^1$ and $X^2$ each are a hydroxyl-protecting group, or $X^1$ and $X^2$ together denote a divalent hydroxyl-protecting group, especially isopropylidene group, a cycloalkylidene group or tetrapyranylidene group.

BEST MODE CARRYING OUT THE INVENTION

The present inventions are illustrated in detail with reference to Examples which demonstrate the preparation of the compound of the general formula (I) according the first aspect of this invention.

However, these Examples are given only by way of example and are not intended to limit this invention in any way. It is needless to mention that various variations and modifications can be made within the scope of this invention.

EXAMPLE 1

(1) Preparation of (2S,3R,4R)-5-(tert-Butoxycarbonylamino)-2,3-O-isopropylidenepentane-1,2,3,4-tetraol (Compound IIIa)

The compound which is prepared according to the method of Kudoh et al. as described in the "J. Antibiotics", 45, p.954–962 (1992), namely (2S,3S,4R)-5-(tert-butoxycarbonylamino)-4-O-(tert-butyldimethylsilyl)-2,3-O-isopropylidenepentane-1,2,3,4-tetraol (Compound IIa)(13.6 g, 33.6 mmol) was dissolved in tetrahydrofuran (200 ml). To the resulting solution was added tetra-n-butylammonium fluoride (1.0M solution in tetrahydrofuran, 67.3 ml). The mixture thus obtained was stirred at room temperature for one hour (for the elimination reaction of the 4-O-tert-butyldimethylsily group). Subsequently, the resulting reaction solution was concentrated under reduced pressure and to the resulting residue was added water. The resultant mixture was extracted three times with chloroform. The combined organic phases were dried over anhydrous magnesium sulfate and then filtered. The resulting filtrate was concentrated under reduced pressure. The residue so obtained was purified by a column chromatography on silica gel with using chloroform-methanol (19:1) as a developing solvent, to afford 9.20 g (94%) of the title compound (Compound IIIa) in the form of a colorless oil.

Specific rotation: $[\alpha]^{27}_D$+37.7° (c 0.94, methanol); $^1$H-NMR spectrum (CD$_3$OD, δ ppm): 1.32 and 1.40 (3H and 3H, each s, CH$_3$ of isopropylidene), 1.43 (9H, s, COOC(CH$_3$)$_3$), 3.40 (1H, dd, J=13.9 and 7.3 Hz, H-5), 3.44 (1H, dd, J=13.9 and 3.4 Hz, H-5), 3.62 (1H, dd, J=11.2 and 6.3 Hz, H-1), 3.71 (1H, ddd, J=9.3, 7.3 and 3.4 Hz, H-4), 3.81 (1H, dd, J=11.2 and 5.9 Hz, H-1), 3.96 (1H, dd, J=9.3 and 6.4 Hz, H-3), 4.25 (1H, br dd, J=12.2 and 6.4 Hz, H-2); IR spectrum (CHCl$_3$): 3450, 2980, 1680, 1510, 1370, 1250, 1160, 1080, 1060 cm$^{-1}$; Mass spectrum (FAB-MS): m/z 292.4 (M+H)$^+$, 236.3, 178.2, 154.1, 136.1, 120.1, 107.1, 57.1.

(2) Preparation of (2S,3R,4R)-5-(tert-Butoxycarbonylamino)-amino)-1-O-(tert-butyldimethylsilyl)-2,3-O-isopropylidenepentane-1,2,3,4-tetraol (Compound IVa)

Compound IIIa (1.0 g, 3.43 mmol), which was obtained in Example 1, step (1) hereinbefore, was dissolved in N,N-dimethylformamide (DMF)(10 ml). To the resulting solution were added imidazole (491 mg, 7.21 mmol) and tert-butyldimethylsilyl chloride (543 mg, 3.60 mmol). The mixture so obtained was stirred at room temperature for two hours (for the reaction for introduction of the 1-O-tert-butyldimethyl-silyl group). Thereafter, the resulting reaction solution was concentrated under reduced pressure and then to the residue thus obtained was added ethyl acetate. The resulting solution was washed twice with water. The organic phase so washed was dried over anhydrous magnesium sulfate and then filtered. The resulting filtrate was concentrated under reduced pressure and thereafter the resulting residue was purified by a column chromatography on silica gel with using n-hexane-ethyl acetate (9:1) as a developing solvent, to afford 1.38 g (99%) of the title compound (Compound IVa) in the form of a colorless oil.

Specific rotation: $[\alpha]^{27}_D$+8.93° (c 0.99, chloroform); $^1$H-NMR spectrum (CD$_3$OD, δ ppm): 0.11 (6H, s, (CH$_3$)$_2$ of t-butyldimethylsilyl), 0.91 (9H, s, (CH$_3$)$_3$ of t-butyl-dimethyl-silyl), 1.31 and 1.40 (3H and 3H, each s, CH$_3$ of isopropylidene), 1.43 (9H, s, COOC(CH$_3$)$_3$), 3.03 (1H, dd, J=13.9 and 7.1 Hz, H-5), 3.44 (1H, dd, J=13.9 and 3.2 Hz, H-5), 3.70–3.77 (2H, m, H-1 and H-4), 3.92–3.98 (2H, m, H-1 and H-3), 4.21 (1H, br dd, J=11.5 and 5.6 Hz, H-2); IR spectrum (CHCl$_3$): 3460, 2940, 1710, 1510, 1370, 1260, 1170, 1080, 840 cm$^{-1}$; Mass spectrum (FAB-MS): m/z 406.3 (M+H)$^+$, 350.2, 306.3, 292.2, 248.2, 142.1, 73.1, 57.1.

(3) Preparation of (2S,3S)-5-(tert-Butoxycarbonylamino)-1-O-(tert-butyldimethylsilyl)-2,3-O-isopropylidene-4-oxopentane-1,2,3-triol (Compound Va)

Compound IVa (5.0 g, 12.3 mmol), which was obtained in Example 1, step (2) hereinbefore, was dissolved in dry dichloromethane (100 ml). To the resulting solution was added the Dess-Martin oxidizing reagent (7.83 g, 18.5 mmol) which was prepared according to the method described in the literature (J. Am. Chem. Soc., 1991, 113, p.7277–7287; J. Org. Chem., 1993, 58, p.2899). The resultant mixture was stirred at room temperature for 4 hours (for the oxidation reaction of the hydroxyl group at the 4-position of Compound IVa). The resulting reaction solution was diluted with chloroform, neutralized with saturated aqueous sodium hydrogen carbonate solution, and filtered with aid of celite to remove insoluble matters therefrom. The resultant filtrate was then separated into two phases. The so separated organic phase was washed with water, dried over anhydrous magnesium sulfate and then filtered. After the resulting filtrate was concentrated under reduced pressure, the residue was added with toluene and the resulting solution containing precipitates deposited therein was filtered to remove the precipitates. After the filtrate obtained was concentrated under reduced pressure, the resulting residue was purified by a column chromatography on silica gel with using n-hexane-ethyl acetate (9:1) as a developing solvent, to afford 4.78 g (96%) of the title compound (Compound Va) in the form of a colorless oil.

Specific rotation: $[\alpha]^{26}_D$−35.8° (c 0.53, methanol); $^1$H-NMR spectrum (CDCl$_3$, δ ppm): 0.03 and 0.04 (3H and 3H, each s, (CH$_3$)$_2$ of t-butyldimethylsilyl), 0.86 (9H, s, (CH$_3$)$_3$ of t-butyldimethylsilyl), 1.35 (3H, s, CH$_3$ of isopropylidene), 1.44 (9H, s, COOC(CH$_3$)$_3$), 1.56 (3H, s, CH$_3$ of isopropylidene), 3.68 (1H, dd, J=11.7 and 2.4 Hz, H-1), 3.75 (1H, dd, J=11.7 and 3.4 Hz, H-1), 4.27 (2H, d, J=4.4 Hz, H-5), 4.38–4.45(1H, m, H-2), 4.56 (1H, d, J=8.3 Hz, H-3), 5.23 (1H, br s, NH); IR spectrum (CHCl$_3$): 3430, 2930, 1700, 1500, 1370, 1250, 1160, 1090, 840 cm$^{-1}$; Mass spectrum (FAB-MS): m/z 404.3 (M+H)$^+$, 348.3, 304.3, 290.2, 246.2, 140.1, 73.1, 57.1.

(4) Preparation of (2S,3S)-5-(tert-Butoxycarbonylamino)-1-O-(tert-butyldimethylsilyl)-2,3-O-isopropylidene-4-methylenepentane-1,2,3-triol (Compound VIa)

Methyltriphenylphosphonium bromide (16.92 g, 47.4 mmol) was suspended into dry tetrahydrofuran (50 ml), and to the suspension thus formed was added lithium bis (trimethylsilyl)-amide (45.0 ml of 1.0 M solution in tetrahydrofuran) under ice-cooling. The mixture thus obtained was stirred at room temperature for 30 minutes. To the resulting reaction solution was added dropwise a solution of Compound Va (4.78 g, 11.8 mmol), which was obtained in Example 1, step (3) as above, and dissolved in dry tetrahydrofuran under ice-cooling. Then, the resulting mixture was stirred under an atmosphere of argon for 30 minutes to effect the reaction (for the Wittig reaction to convert the oxo group at the 4-position of the Compound Va into methylene group). Thereafter, to the resulting reaction solution was added acetic acid (2.94 ml, 47.4 mmol) under ice-cooling to terminate the reaction, and the resulting mixture was stirred for further 30 minutes.

After the reaction solution so obtained was concentrated under reduced pressure, the resulting residue was added with water and the resulting solution was extracted twice with chloroform. The resulting organic phases (the chloroform extracts) were combined and dried over anhydrous magnesium sulfate and then filtered. The filtrate obtained was concentrated under reduced pressure, and the resulting residue was purified by a column chromatography on silica gel with using n-hexane-ethyl acetate (9:1) as a developing solvent, to afford 3.83 g (81%) of the title compound (Compound VIa) in the form of a colorless oil.

Specific rotation: $[\alpha]^{28}_D$ –43.5° (c 0.87, chloroform); $^1$H-NMR spectrum (CDCl$_3$, δ ppm): 0.04 and 0.06 (3H and 3H, each s, (CH$_3$)$_2$ of t-butyldimethylsilyl), 0.88(9H, s, (CH$_3$)$_3$ of t-butyl-dimethylsilyl), 1.36 (3H, s, CH$_3$ of isopropylidene), 1.44 (12H, s, CH$_3$ of isopropylidene and COOC(CH$_3$)$_3$), 3.44 (1H, dd, J=9.8 and 3.9 Hz, H-1), 3.55 (1H, br t, J=9.5 Hz, H-1), 3.69 (1H, dd, J=15.1 and 3.9 Hz, H-5), 3.94 (1H, dd, J=15.1 and 6.8 Hz, H-5), 4.18–4.23 (1H, m, H-2), 4.66 (1H, d, J=5.9 Hz, H-3), 5.15 and 5.33 (1H and 1H, each br s, H$_2$C=C), 5.39 (1H, br s, NH); IR spectrum (KBr): 3450, 3350, 2950, 1710, 1510, 1370, 1250, 1170, 1080, 840 cm$^{-1}$; Mass spectrum (FAB-MS): m/z 402.3 (M+H)$^+$, 346.3, 330.2, 288.2, 230.1, 226.3, 186.2, 154.1, 138.1, 73.1, 57.1.

(5) Preparation of (2S,3S)-5-(tert-Butoxycarbonylamino)-2,3-O-isopropylidene-4-methylenepentane-1,2,3-triol (Compound VIIa)

Compound VIa (8.28 g, 20.6 mmol), which was obtained in Example 1, step (4) as above, was dissolved in dry tetrahydrofuran (100 ml). To the resulting solution was added tetra-n-butylammonium fluoride (24.7 ml as a 1.0 M solution in tetrahydrofuran). The mixture obtained was stirred at room temperature for 30 minutes to effect the reaction (for the elimination of 1-O-tert-butyldimethylsilyl group). Thereafter, the resulting reaction solution was concentrated under reduced pressure and the residue was added with water. The resulting solution was washed three times with chloroform. The organic phases (the chloroform extracts) obtained were combined and dried over anhydrous magnesium sulfate and then filtered. After the filtrate was concentrated under reduced pressure, the resulting residue was purified by a column chromatography on silica gel with using chloroform-methanol (24:1) as a developing solvent, to afford 5.98 g (99%) of the title compound (Compound VIIa) in the form of a colorless oil.

Specific rotation: $[\alpha]^{28}_D$ –49.3° (c 0.94, chloroform); $^1$H-NMR spectrum (CDCl$_3$, δ ppm): 1.38 (3H, s, CH$_3$ of isopropylidene), 1.45 (9H, s, COOC(CH$_3$)$_3$), 1.49 (3H, s, CH$_3$ of isopropylidene), 2.93 (1H, br t, J=6.3 Hz, —OH), 3.49 (1H, br quintet, J=5.9 Hz, H-1), 3.56–3.65 (1H, m, H-1), 3.69 (1H, dd, J=16.8 and 6.1 Hz, H-5), 3.81 (1H, dd, J=16.8 and 5.9 Hz, H-5), 4.31 (1H, br dd, J=6.3 and 5.9 Hz, H-2), 4.68 (1H, d, J=6.3 Hz, H-3), 4.93 (1H, br s, NH), 5.17 and 5.33 (1H and 1H, br s, H$_2$C=C); IR spectrum (CHCl$_3$): 3470, 3000, 1710, 1520, 1380, 1250, 1170, 1040 cm$^{-1}$; Mass spectrum (FAB-MS): m/z 288.3 (M+H)$^+$, 232.2, 174.2, 154.1, 112.1, 57.1.

(6) Preparation of (2R,3R,4S)-1-N-(tert-Butoxycarbonylamino)-3,4-O-isopropylidene-5-methylenepiperidine-2,3,4-triol (Compound VIIIa)

To a solution of oxalyl chloride (1.09 ml, 12.5 mmol) in dry dichloromethane (20 ml) was added at –78° C. a solution of dimethyl sulfoxide (1.78 ml, 25.1 mmol) dissolved in dry dichloromethane (20 ml). The resulting mixture was stirred at –78° C. for 20 minutes. To the resulting reaction solution was added dropwise a solution of Compound VIIa (900 mg, 33 mmol), which was obtained in Example 1, step (5) as above, dissolved in anhydrous dichloromethane (10 ml) at the same temperature as above. The mixture obtained was stirred for 20 minutes. The resulting mixture was added with triethylamine (8.73 ml, 62.6 mmol) dropwise and then stirred at room temperature for one hour, to effect the reactions (for the reaction to oxidize the hydroxyl group at the 1-position of the Compound VIIa with accompanying cyclization). Thereafter, the resulting reaction solution was added with water to terminate the reactions, and the mixture so obtained was stirred for 30 minutes. The resulting solution was diluted with chloroform and washed with water. The organic phase was separated, dried over anhydrous magnesium sulfate and filtered. After the filtrate was concentrated under reduced pressure, the residue obtained was purified by a column chromatography on silica gel with using toluene-acetone (19:1) as a developing solvent, to afford 734 mg (82%) of the title compound (Compound VIIIa) in the form of a colorless powder.

Specific rotation: $[\alpha]^{29}_D$ –9.93° (c 0.45, chloroform); $^1$H-NMR spectrum (CDCl$_3$, δ ppm): 1.37 and 1.44 (3H and 3H, each s, CH$_3$ of isopropylidene), 1.48 (9H, s, COOC (CH$_3$)$_3$), 3.17 (1H, br s, —OH), 3.82 (1H, d, J=14.2 Hz, H-6), 4.19 (1H, d, J=14.2 Hz, H-6), 4.41 (1H, dd, J=2.0 and 7.3 Hz, H-3), 4.74 (1H, d, J=7.3 Hz, H-4), 5.25 and 5.33 (1H and 1H, each br S, H$_2$C=C), 5.68 (1H, br s, H-2); IR spectrum (CDCl$_3$): 3400, 2980, 2940, 1690, 1400, 1365, 1340, 1300, 1260, 1170, 1060, 1020, 920, 880 cm$^{-1}$; Mass spectrum (FAB-MS): m/z 286 (M+H)$^+$, 271.1, 268.2, 230.1, 212.1, 168.1, 154.1, 110, 57.1.

(7) Preparation of (2S,3S,4S)-1-N-(tert-Butoxycarbonyl)-3,4-O-isopropylidene-5-methylene-2-phthalimidopiperidine-3,4-diol (Compound IXa)

Compound VIIIa (500 mg, 1.75 mmol), which was obtained in Example 1, step (6) as above, was dissolved in dry DMF (10 ml). To the resulting solution were added triphenylphosphine (1.38 g, 5.26 mmol), phthalimide (773 mg, 5.26 mmol) and diethyl azodicarboxylate (0.837 ml, 5.26 mmol) under ice-cooling. The resultant mixture was stirred at room temperature for 12 hours to effect the reaction (for conducting the Mitsunobu reaction on the hydroxyl group at the 2-position of Compound VIIIa). Thereafter, the resulting reaction solution was added with water (3 ml) to terminate the reaction, and then the resulting reaction solution was concentrated under reduced pressure. To the resulting residue was added ethyl acetate. The solution obtained was washed twice with a saturated aqueous sodium chloride solution. The organic phase was separated, dried over anhydrous magnesium sulfate and then filtered. After the resulting filtrate was concentrated under reduced pressure, the residue so obtained was purified by a column chromatography on silica gel with using toluene-ethyl acetate (19:1) as a developing solvent, to afford 692 mg (95%) of the title compound (Compound IX) in the form of a colorless foam.

Specific rotation: $[\alpha]^{28}_D$+57.6° (c 0.85, chloroform); $^1$H-NMR spectrum (CDCl$_3$, δ ppm): 1.40 (3H, s, CH$_3$ of isopropylidene), 1.49 (12H, s, CH$_3$ of isopropylidene and COOC(CH$_3$)$_3$), 3.82 (1H, d, J=14.7 Hz, H-6), 4.48 (1H, d, J=14.7 Hz, H-6), 4.75 (1H, d, J=6.4 Hz, H-3), 5.00 (1H, d, J=6.4 Hz, H-4), 5.19 and 5.32 (1H and 1H, each br s, H$_2$C=C), 6.35(1H, br s with a small coupling, H-2), 7.72–7.84 (4H, m, phthalimido); IR spectrum (CHCl$_3$): 2950, 2920, 1775, 1720, 1470, 1450, 1370, 1160, 1120, 1070, 900 cm$^{-1}$; Mass spectrum (FAB-MS): m/z 415.3 (M+H)$^+$, 359.2, 315.2, 168.2, 148.1, 110.1, 57.1.

(8) Preparation of (2S,3S,4R,5R)-1-N-(tert-Butoxycarbonyl)-3,4-O-isopropylidene-5-methyl-2-phthalimidopiperidine-3,4-diol (Compound Xa)

Compound IXa (3.69 g, 8.69 mmol), which was obtained in Example 1, step (7) as above, was dissolved in methanol (200 ml). To the resulting solution was added a catalyst of 10% palladium on carbon (1.0 g), and then the resultant mixture was stirred at room temperature under an atmosphere of hydrogen for 5 hours to effect the catalytic reduction (for the reaction to convert the 5-methylene group into methyl group). The resulting reaction solution was filtered with aid of celite, to remove the catalyst of 10% palladium on carbon therefrom, and the filtrate obtained was concentrated under reduced pressure. The residue obtained was purified by a column chromatography on silica gel with using toluene-ethyl acetate (9:1) as a developing solvent, to afford 2.73 g (75%) of the title compound (Compound Xa) in the form of a colorless foam.

Specific rotation: $[\alpha]^{26}_D$-32.9° (c 0.49, chloroform); $^1$H-NMR spectrum (CDCl$_3$, δ ppm): 1.08 (3H, d, J=6.8 Hz, CH$_3$), 1.36 (3H, s, CH$_3$ of isopropylidene), 1.38 (9H, s, COOC(CH$_3$)$_3$), 1.48 (3H, s, CH$_3$ of isopropylidene), 2.34–2.44 (1H, m, H-5), 3.19 (1H, br t, J=11.5 Hz, H-6ax), 3.50 (1H, dd, J=11.5 and 4.6 Hz, H-6eq), 4.33 (1H, dd, J=7.3 and 3.4 Hz, H-4), 4.63 (1H, dd, J=7.3 and 2.0 Hz, H-3), 6.05 (1H, d, J=2.0 Hz, H-2), 7.71–7.83 (4H, m, phthalimido); IR spectrum (KBr): 3450, 2980, 1770, 1720, 1700, 1610, 1470, 1410, 1370, 1340, 1270, 1160, 1120, 1060, 1020, 900, 720 cm$^{-1}$; Mass spectrum (FAB-MS): m/z 417.3 (M+H)$^+$, 361.2, 317.2, 214.2, 170.2, 148.1, 112.1, 57.1

(9) Preparation of (2R,3S,4R,5R)-2-amino-1-N-(tert-Butoxycarbonyl)-3,4-O-isopropylidene-5-methylpiperidine-3,4-diol (Compound XIa)

Compound Xa (83 mg, 0.20 mmol), which was obtained in Example 1, step (8) as above, was dissolved in methanol (5 ml). To the resulting solution was added hydrazine hydrate (H$_2$NNH$_2$.xH$_2$O, 0.5 ml), and the resultant mixture was stirred at room temperature for 12 hours to effect the reaction (for elimination of the phthaloyl group). The resulting reaction solution containing precipitates deposited therein was filtrated and then the filtrate was concentrated under reduced pressure. To the residue obtained was added water. The resultant solution was extracted three times with chloroform. The resulting organic phases (the chloroform extracts) were combined, dried over anhydrous magnesium sulfate and filtered. After the filtrate obtained was concentrated under reduced pressure, the resulting residue was purified by a column chromatography on silica gel with using chloroform-methanol (25:1) as a developing solvent, to afford 57 mg (99%) of the title compound (Compound XI) in the form of a colorless foam.

Specific rotation: $[\alpha]^{28}_D$+14.3° (c 1.27, chloroform); $^1$H-NMR spectrum (CD$_3$OD, δ ppm): 1.00 (3H, d, J=6.8 Hz, —CH$_3$), 1.31 and 1.35 (3H and 3H, each s, CH$_3$ of isopropylidene), 1.47 (9H, s, COOC(CH$_3$)$_3$), 2.28–2.38 (1H, m, H-5), 2.99 (1H, br t, J=12.2 Hz, H-6ax), 3.22 (1H, dd with a small coupling, J=12.2 and 4.9 Hz, H-6eq), 4.30 (1H, dd with a small coupling, J=7.8 and 2.4 Hz, H-4), 4.33 (1H, dd, J=7.8 and 1.5 Hz, H-3), 4.90 (1H, d, J=1.5 Hz, H-2); IR spectrum (CHCl$_3$): 2970, 1680, 1470, 1450, 1360, 1260, 1160, 1105, 1010 cm$^{-1}$; Mass spectrum (FAB-MS): m/z 287 (M+H)$^+$, 270.2, 214.2, 170.1, 112.1, 57.

(10) Preparation of (2S,3S,4R,5R)-2-Acetamido-1-N-(tert-butoxycarbonyl)-3,4-O-isopropylidene-5-methyl-piperidine-3,4-diol (Compound XIIa)

To Compound XIa (20 mg, 0.0698 mmol), which was obtained in Example 1, step (9) as above, were added pyridine (0.5 ml), acetic anhydride (0.5 ml) and 4-dimethylaminopyridine (2 mg), and then the resultant mixture was stirred at room temperature for 12 hours (for the acetylation reaction of the amino group at the 2-position of Compound XIa). After the resulting reaction solution was concentrated under reduced pressure, the residue was added with ethyl acetate. The resulting solution was washed twice with a saturated aqueous sodium chloride solution. The organic phase so washed was dried over anhydrous magnesium sulfate and then filtered. The filtrate obtained was concentrated under reduced pressure, and the resulting residue was purified by a column chromatography on silica gel with using toluene-acetone (3:1) as a developing solvent, to afford 23 mg (99%) of the title compound (Compound XIIa) in the form of a colorless foam.

Specific rotation: $[\alpha]^{27}_D$-34.3° (c 0.57, chloroform); $^1$H-NMR spectrum (CDCl$_3$, δ ppm): 1.05 (3H, d, J=6.8 Hz, —CH$_3$), 1.33 and 1.50 (3H and 3H, each s, CH$_3$ of isopropylidene), 1.46 (9H, s, COOC(CH$_3$)$_3$), 1.98 (3H, s, —NHCOC$\underline{H}_3$), 1.88–2.01 (1H, m, H-5), 3.01 (1H, br t, J=12.5 Hz, H-6ax), 3.32 (1H, dd, J=12.2 and 3.9 Hz, H-6eq), 4.26 (1H, dd, J=7.3 and 2.0 Hz, H-4), 4.53 (1H, br d with a small coupling, J=7.3 Hz, H-3), 5.73 (2H, br s, H-2 and NH); IR spectrum (CHCl$_3$): 3450, 2990, 1680, 1490, 1390, 1370, 1260, 1170, 1070, 1020 cm$^{-1}$; Mass spectrum (FAB-MS): m/z 329.3 (M+H)$^+$, 273.2, 214.2, 170.2, 154.1, 112.1, 57.1.

(11) Preparation of Hydrochloride of (2S,3S,4R,5R)-2-Acetamido-5-methylpiperidine-3,4-diol (Compound Ia)

Compound XIIa (10 mg, 0.0304 mmol), which was obtained in Example 1, step (10) as above, was dissolved in diethyl ether (1 ml). To the resulting solution was added 4N hydrochloric acid—dioxane solution (0.2 ml) under ice-cooling, and the resultant mixture was stirred 3 hours (for the elimination reaction of both the 3,4-O-isopropylidene group and the amino-protecting group at the 1-position of Compound XIIa). To the resulting reaction solution containing colorless solids as deposited and suspended therein, there was further added diethyl ether. The resultant mixture was stirred thoroughly. Thereafter, the resulting solution containing colorless solids as deposited therein was centrifuged to allow the solids to precipitate well, and then the supernatant was removed. The precipitates thus obtained were dried under reduced pressure, to afford 4.4 mg (65%) of a hydrochloride of the title compound (Compound Ia) in the form of a colorless solid.

Specific rotation: $[\alpha]^{27}_D$-32.3° (c 0.41, methanol); $^1$H-NMR spectrum (CD$_3$OD, δ ppm): 1.05 (3H, d, J=6.8 Hz, —CH$_3$), 1.95–2.06 (1H, m, H-5), 2.05 (3H, s, —NHCO CH$_3$), 2.92 (1H, dd, J=12.2 and 3.9 Hz, H-6eq), 3.05 (1H, br t, J=12.5 Hz, H-6ax), 3.72 (1H, dd, J=10.3 and 2.4 Hz, H-3), 3.84–3.87 (1H, m, H-4), 4.91 (1H, d, J=10.3 Hz, H-2); IR spectrum (KBr): 3325, 1660, 1460, 1400, 1140, 1060, 910 CM$^{-1}$; Mass spectrum (FAB-MS): m/z 189.2 (M+H)$^+$, 176.1, 154.1, 137.1, 120.1, 107, 89, 77.

EXAMPLE 2

(1) Preparation of (2S,3S,4R,5R)-1-N-(tert-Butoxycarbonyl)-2-trifluoroacetamido-3,4-O-isopropylidene-5-methylpiperidine-3,4-diol (Compound XIIb)

Compound XIa (120 mg, 0.419 mmol), which was obtained in Example 1, step (9) as above, was dissolved in dry dichloromethane (2 ml). To the resulting solution were added pyridine (0.1 ml), trifluoroacetic anhydride (0.1 ml) and 4-dimethylaminopyridine (10 mg) under ice-cooling, and the resultant mixture was stirred for 30 minutes (for the trifluoroacetylation reaction of the amino group at the 2-position of Compound XIa). After the resulting reaction solution was concentrated under reduced pressure, the residue was added with ethyl acetate. The resulting solution was washed twice with a saturated aqueous sodium chloride solution. The organic phase (the solution in ethyl acetate) so washed was dried over anhydrous magnesium sulfate and then filtered. The filtrate obtained was concentrated under reduced pressure, and the resulting residue was purified by a column chromatography on silica gel with using toluene-ethyl acetate (10:1) as a developing solvent, to afford 159 mg (99%) of the title compound (Compound XIIb) in the form of a colorless powder.

Specific rotation: [α]$^{25}_D$–37.2° (c 0.46, chloroform); $^1$H-NMR spectrum (CDCl$_3$, δ ppm): 1.08 (3H, d, J=6.8 Hz, —CH$_3$), 1.35 (3H, s, CH$_3$ of isopropylidene), 1.46 (12H, s, CH$_3$ of isopropylidene and COOC(CH$_3$)$_3$), 1.82–1.95 (1H, m, H-5), 3.01 (1H, br t, J=12.5 Hz, H-6ax), 3.39 (1H, dd, J=12.2 and 3.9 Hz, H-6eq), 4.32 (1H, dd, J=6.8 and 2.4 Hz, H-4), 4.52 (1H, br d with a small coupling, H-3), 5.77(1H, br s, H-2); IR spectrum CHCl$_3$): 3280, 2980, 1720, 1680, 1530, 1390, 1320, 1210, 1160, 1070, 1010, 860 cm$^{-1}$; Mass spectrum (FAB-MS): m/z 383.2 (M+H)$^+$, 327.2, 214.2, 170.2, 154.1, 112.1, 57.1.

(2) Preparation of Hydrochloride of (2S,3S,4R,5R)-2-Trifluoroacetamido-5-methylpiperidine-3,4-diol (Compound Ib)

Compound XIIb (15 mg, 0.0392 mmol), which was obtained in Example 2, step (1) above, was dissolved in dry dioxane (0.5 ml). To the resulting solution was added 4N hydrochloric acid—dioxane solution (0.2 ml), and then the resultant mixture was stirred at room temperature one hour. Thereafter, to the solution so obtained was added further 4N hydrochloric acid—dioxane solution (0.2 ml), and then the resultant mixture was stirred at room temperature for two hours (for the elimination reaction of the tert-butoxycarbonyl group and the 3,4-O-isopropylidene group of Compound XIIb). To the resulting reaction solution containing colorless solids deposited and suspended therein, there was added diethyl ether. The resulting mixture was stirred thoroughly. Subsequently, the resulting solution containing colorless solids as deposited therein was centrifuged to allow the solids to precipitate well, and then the supernatant was removed. The precipitates thus recovered were dried under reduced pressure, to afford 11 mg (97%) of a hydrochloride of the title compound (Compound Ib) in the form of a colorless solid.

Specific rotation: [α]$^{28}_D$–42.3° (c 0.46, methanol); $^1$H-NMR spectrum (CD$_3$OD, δ ppm): 1.06 (3H, d, J=6.8 Hz, —CH$_3$), 1.95–2.06(1H, m, H-5), 2.97 (1H, dd, J=12.2 and 4.4 Hz, H-6eq), 3.09 (1H, br t, J=12 Hz, H-6ax), 3.84 (1H, dd, J=10.3 and 2.4 Hz, H-3), 3.87–3.90 (1H, m, H-4), 4.99 (1H, d, J=10.3 Hz, H-2); IR spectrum (KBr): 3440, 3250, 2950, 2780, 1730, 1555, 1400, 1260, 1220, 1180, 1100, 990, 900 cm$^{-1}$; Mass spectrum (FAB-MS): m/z 243.2 (M+H)$^+$, 154.1, 137.1, 120.1, 107.1, 89, 77.

EXAMPLE 3

(1) Preparation of (2S,3S,4R,5R)-1-N-(tert-Butoxycarbonyl)-2-trichloroacetamido-3,4-O-isopropylidene-5-methylpiperidine-3,4-diol (Compound XIIc)

Compound XIa (17 mg, 0.0593 mmol), which was obtained in Example 1, step (9) above, was dissolved in dry dichloromethane (3 ml). To the resulting solution were added pyridine (19.2 μl, 0.238 mmol) and trichloroacetyl chloride (13.3 μl, 0.119 mmol) under ice-cooling. Then, the resultant mixture was stirred for 30 minutes (for the trichloroacetylation reaction of the amino group at the 2-position of Compound XIa). The resulting reaction solution was added with dichloromethane (15 ml) and washed with water, and thereafter the organic phase thus washed was dried over anhydrous magnesium sulfate and then filtered. The filtrate obtained was concentrated under reduced pressure, and the resulting residue was purified by a column chromatography on silica gel with using toluene-ethyl acetate (10:1) as a developing solvent, to afford 25.6 mg (99%) of the title compound (Compound XIIc) in the form of a colorless foam.

$^1$H-NMR spectrum (CD$_3$OD, δ ppm): 1.08 (3H, d, J=6.8 Hz, —CH$_3$), 1.36 (3H, s, CH$_3$ of isopropylidene), 1.47 (12H, s, COOC(CH$_3$)3 and CH$_3$ of isopropylidene), 1.81–1.93 (1H, m, H-5), 3.01 (1H, br t, J=12.5 Hz, H-6ax), 3.42 (1H, dd, J=11.7 and 3.4 Hz, H-6eq), 4.34 (1H, dd, J=7.3 and 2.0 Hz, H-4), 4.56(1H, br d, J=5.4 Hz, H-3), 5.75 (1H, br s, H-2), 6.60 (1H, br s, NH); Mass spectrum (FAB-MS): m/z 433 (M+2H)$^+$, 431 (M)$^+$, 377, 375.16, 359.15, 270.31, 214.26, 170.24, 154.16, 57.10.

(2) Preparation of Hydrochloride of (2S,3S,4R,5R)-2-Trichloroacetamido-5-methylpiperidine-3,4-diol (Compound Ic)

Compound XIIc (15 mg, 0.0347 mmol), which was obtained in Example 3, step (1) above, was dissolved in dry dioxane (0.5 ml). To the resulting solution was added 4N hydrochloric acid—dioxane solution (0.2 ml), and the resultant mixture was stirred at room temperature for two hours (for the elimination reaction of the tert-butoxycarbonyl group and the 3,4-O-isopropylidene group of Compound XIIc). To the resulting reaction solution containing colorless solids as deposited and suspended therein, diethyl ether was added. The resultant mixture was stirred thoroughly. Thereafter, the mixture was centrifuged to allow the solids to precipitate well, and the supernatant was removed. The precipitates thus recovered were dried under reduced pressure, to afford 8.8 mg (77%) of a hydrochloride of the title compound (Compound Ic) in the form of a colorless solid.

Specific rotation: [α]$^{23}_D$–37.80 (c 0.23, methanol); $^1$H-NMR spectrum (CD$_3$OD, δ ppm): 1.07 (3H, d, J=6.8 Hz, —CH₃), 1.96–2.02 (1H, m, H-5), 2.99 (1H, dd, J=12.2 and 4.4 Hz, H-6eq), 3.07 (1H, br t, J=12 Hz, H-6ax), 3.88–3.91 (1H, m, H-4), 3.94 (1H, dd, J=10.3 and 2.4 Hz, H-3), 4.97 (1H, d, J=10.3 Hz, H-2); Mass spectrum (FAB-MS): m/z 293 (M+H)⁺, 291.08 (M)⁺, 170.18, 154.09, 136.09, 130.13, 112.06, 107.04, 89.03, 77.04.

EXAMPLE 4

Preparation of Hydrochloride of (2S,3S,4R,5R)-5-Methyl-2-phtalimidopiperidine-3,4-diol (Compound Id)

Compound Xa as obtained in Example 1, step (8) hereinbefore, namely (2S,3S,4R,5R)-1-N-(tert-butoxycarbonyl)-3,4-O-isopropylidene-5-methyl-2-phthalimidopiperidine-3,4-diol (20 mg, 0.048 mmol) was dissolved in dry dioxane (0.5 ml). To the resulting solution was added 4N hydrochloric acid—dioxane solution (0.2 ml), and the resultant mixture was stirred at room temperature for two hours. Subsequently, to the resulting mixture was added further 4N hydrochloric acid—dioxane solution (0.5 ml). The resultant mixture was stirred at room temperature for 1.5 hours (for the elimination reaction of both the tert-butoxycarbonyl group and the 3,4-O-isopropylidene group of Compound Xa). To the resulting reaction solution containing colorless solids as deposited and suspended therein, there was added diethyl ether. The resultant mixture was stirred thoroughly. Thereafter, the mixture was centrifuged to allow the solids to precipitate well, and the supernatant was removed. The precipitates thus recovered were dried under reduced pressure, to afford 14.1 mg (77%) of a hydrochloride of the title compound (Compound Id) in the form of a colorless solid.

Specific rotation: $[\alpha]^{23}_D$ –19.6° (c 0.25, methanol); ¹H-NMR spectrum (CD₃OD, δ ppm): 1.11 (3H, d, J=6.8 Hz, —CH₃), 2.14–2.23(1H, m, H-5), 3.10 (1H, dd, J=12.2 and 4.4 Hz, H-6eq), 3.23 (1H, br t, J=12 Hz, H-6ax), 3.99 (1H, br s, H-4), 4.54 (1H, dd, J=10.3 and 2.4 Hz, H-3), 5.44 (1H, d, J=10.3 Hz, H-2), 7.88–8.00 (4H, m, phthalimido); Mass spectrum (FAB-MS): m/z 277.19 (M+H)⁺, 265.17, 202.22, 170.17, 1540.10, 136.09, 130.13, 107.04, 89.03, 77.04.

EXAMPLE 5

Preparation of (2R,3S,4R,5R)-2-Amino-5-methylpiperidine-3,4-diol (Compound Ie)

(1) Compound XIa as obtained in Example 1, step (9) hereinbefore, namely (2R,3S,4R,5R)-2-amino-1-N-(tert-butoxycarbonyl)-3,4-O-isopropylidene-5-methylpiperidine-3,4-diol was dissolved in dry dioxane. The resulting solution was treated with 4N hydrochloric acid—dioxane solution in the same manner as described in Example 4. The resultant mixture was after-treated in the same manner as described in Example 4. The title compound (Compound Ie) was thus obtained in the form of a colorless solid.

(2) Compound Ib as obtained in Example 2, step (2) hereinbefore, namely (2S,3S,4R,5R)-2-trifluoroacetamido-5-methylpiperidine-3,4-diol was dissolved in methanol and the resultant solution was stirred at 50° C. for 13 hours. Thereafter, the resulting reaction solution was concentrated under reduced pressure, to afford a hydrochloride of the title compound (Compound Ie) in the form of a colorless oil.

Specific rotation: $[\alpha]^{27}_D$ –24.9° (c 0.15, methanol); ¹H-NMR spectrum (CD₃OD, δ ppm): 1.04 (3H, d, J=6.8 Hz, —CH₃), 1.95–2.02 (1H, m, H-5), 2.99–3.04 (2H, m, H-6), 3.55 (1H, dd, J=2.5 and 8.8 Hz, H-3), 3.84 (1H, br t, J=2.5 Hz, H-4), 4.42(1H, d, J=8.8 Hz,H-2); ¹³C-NMR spectrum (CD₃OD, δ ppm): 14.21 (CH₃), 33.52 (C-5), 44.26 (C-6), 72.25 (C-3 or C-4), 72.99 (C-4 or C-3), 88.86 (C-2); Mass spectrum (FAB-MS): m/z 130.2 (M-NH₃+H)⁺, 107.0, 89.0, 77.1.

Industrial Applicability

As will be apparent from the foregoing descriptions, (2R,3S,4R,5R)-2-amino-5-methylpiperidine-3,4-diol or the (2S,3S,4R,5R)-2-N-substituted-2-amino-5-methylpiperidine-3,4-diol of the general formula (I) according to this invention is provided by the novel process.

These novel compounds of this invention each have a potent enzyme-inhibitory activity against glycosidases, especially fucosidase and glucosidase, so that they are useful as medicines for various applications.

What is claimed is:

1. (2R,3S,4R,5R)-2-Amino-5-methylpiperidine-3,4-diol or a (2S,3S,4R,5R)-2-N-substituted-2-amino-5-methylpiperidine-3,4-diol represented by formula (I):

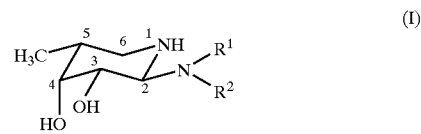

(I)

wherein R¹ and R² each are a hydrogen atom, or R¹ is a hydrogen atom and R² is a lower alkanoyl group or a lower ω-trihaloalkanoyl group, or R¹ and R² together denote a phthaloyl group, or a pharmaceutically acceptable salt thereof.

2. A compound according to claim 1, which is represented by formula (Ia):

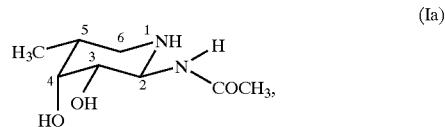

(Ia)

namely (2S,3S,4R,5R)-2-acetamido-5-methylpiperidine-3,4-diol.

3. A compound according to claim 1, which is represented by formula (Ib):

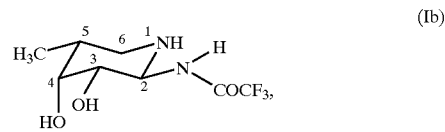

(Ib)

namely (2S,3S,4R,5R)-2-trifluoroacetamido-5-methylpiperidine-3,4-diol.

4. A compound according to claim 1, which is represented by formula (Ic):

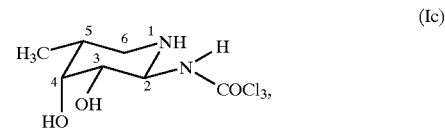

(Ic)

namely (2S,3S,4R, 5R)-2-trichloroacetamido-5-methylpiperidine-3,4-diol.

5. A compound according to claim 1, which is represented by formula (Id):

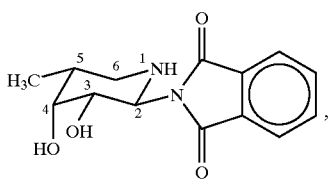

(Id)

group, namely (2S,3S,4R,5R)-2-phthalimido-5-methylpiperidine-3,4-diol.

6. A compound according to claim 1, which is represented by formula (Ie):

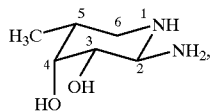

(Ie)

namely (2R,3S,4R,5R)-2-amino-5-methylpiperidine-3,4-diol.

7. A compound according to claim 1 selected from the group consisting of (2R,3S,4R,5R)-2-amino-5-methylpiperidine-3,4-diol or a (2S,3S,4R,5R)-2-N-substituted-2-amino-5-methylpiperidine-3,4-diol represented by formula (I), or a pharmaceutically acceptable salt thereof.

8. A pharmaceutical composition comprising as an active ingredient a therapeutically effective amount of (2R,3S,4R,5R)-2-amino-5-methylpiperidine-3,4-diol or a (2S,3S,4R,5R)-2-N-substituted-2-amino-5-methylpiperidine-3,4-diol represented by formula (I) according to claim 1, or a pharmaceutically acceptable salt thereof, in combination with a pharmaceutically acceptable carrier.

9. A glycosidase inhibitory composition comprising a (2R,3S,4R,5R)-2-amino-5-methylpiperidine-3,4-diol or a (2S,3S,4R,5R)-2-N-substituted-2-amino-5-methylpiperidine-3,4-diol represented by formula (I) according to claim 1, and a pharmaceutically acceptable carrier.

10. A (2S,3S,4S)-1-N-protected-3,4-O-di-protected-5-methylene-2-phthalimidopiperidine-3,4-diol represented by formula (IX):

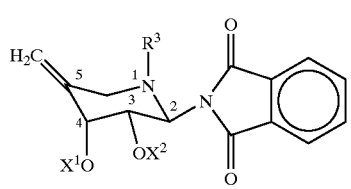

(IX)

wherein $R^3$ is an imino-protecting group, and $X^1$ and $X^2$ each are a hydroxyl-protecting group, or $X^1$ and $X^2$ together denote a divalent hydroxyl-protecting group.

11. A (2S,3S,4S)-1-N-protected-3,4-O-di-protected-5-methylene-2-phthalimidopiperidine-3,4-diol according to claim 10 wherein the imino-protecting group is a tert-butoxycarbonyl group.

12. A (2S,3S,4S)-1-N-protected-3,4-O-di-protected-5-methylene-2-phthalimidopiperidine-3,4-diol according to claim 10 wherein the hydroxyl-protecting group is selected from the group consisting of an isopropylidene group, a cycloalkylidene group and a tetrapyranylidene group.

13. A process for the preparation of (2R,3S,4R,5R)-2-amino-5-methylpiperidine-3,4-diol or a (2S,3S,4R,5R)-2-N-substituted-2-amino-5-methylpiperidine-3,4-diol represented by formula (I):

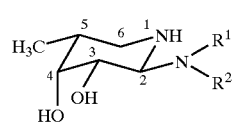

(I)

wherein $R^1$ and $R^2$ each are a hydrogen atom, or $R^1$ is a hydrogen atom and $R^2$ is a lower alkanoyl group or a lower ω-trihaloalkanoyl group, or $R^1$ and $R^2$ together denote phthaloyl group, characterized in that the process comprises:

eliminating the hydroxyl-protecting group ($R_4$) at the 4-position of a (2S,3S or 3R,4R)-5-N-protected-2,3,4-O-tri-protected-5-aminopentane-1,2,3,4-tetraol represented by formula (II):

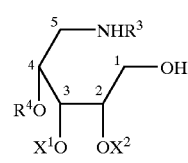

(II)

wherein $R^3$ is an amino-protecting group, $R^4$ is a hydroxyl-protecting group, and $X^1$ and $X^2$ each are a hydroxyl-protecting group, or $X^1$ and $X^2$ together denote one divalent hydroxyl-protecting group having the formula:

where $R^5$ and $R^6$ may be the same or different and each denote a hydrogen atom, an alkyl group or an aryl group, especially phenyl group, or $X^1$ and $X^2$ together denote a cycloalkylidene group or tetrapyranylidene group, to give a (2S,3R,4R)-5-N-protected-2,3-O-di-protected-5-aminopentane-1,2,3,4-tetraol represented by formula (III):

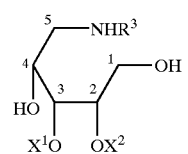

(III)

wherein $R^3$, $X^1$ and $X^2$ have the same meanings as above;

protecting the hydroxyl group at the 1-position of the compound of formula (III) with a hydroxyl-protecting group ($R^7$), to prepare a (2S,3R,4R)-5-N-protected-1, 2,3-O-tri-protected-5-aminopentane-1,2,3,4-tetraol represented by formula (IV):

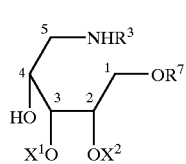

(IV)

wherein $R^3$, $X^1$ and $X^2$ have the same meanings as above and $R^7$ denotes a hydroxyl-protecting group;

oxidizing the hydroxyl group at the 4-position of the compound of formula (IV), to prepare a (2S,3S)-5-N-protected-1,2,3-O-tri-protected-4-keto-5-aminopentane-1,2,3-triol represented by formula (V):

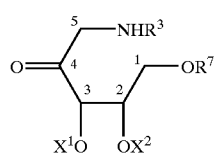

(V)

wherein $R^3$, $X^1$, $X^2$ and $R^7$ have the same meanings as above;

subjecting the oxo group at the 4-position of the compound of formula (V) to the Wittig reaction so as to convert the oxo group into a methylene group, thereby producing a (2S,3S)-5-N-protected-1,2,3-O-tri-protected-4-methylene-5-aminopentane-1,2,3-triol represented by formula (VI):

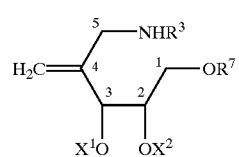

(VI)

wherein $R^3$, $R^7$, $X^1$ and $X^2$ have the same meanings as above;

eliminating the hydroxyl-protecting group ($R^7$) at the 1-position of the compound of formula (VI), to prepare a (2S,3S)-5-N-protected-2,3-O-di-protected-4-methylene-5-aminopentane-1,2,3-triol represented by formula (VII):

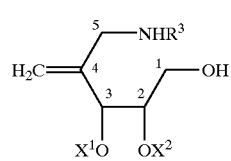

(VII)

wherein $R^3$, $X^1$ and $X^2$ have the same meanings as above;

oxidizing the hydroxyl group at the 1-position of the compound of formula (VII) with accompanying cyclization, to prepare a (2R,3R,4S)-1-N-protected-3,4-O-di-protected-5-methylenepiperidine-2,3,4-triol represented by formula (VIII):

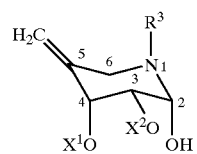

(VIII)

wherein $R^3$, $X^1$ and $X^2$ have the same meanings as above;

conducting the Mitsunobu reaction on the hydroxyl group at the 2-position of the compound of formula (VIII) by reaction with phthalimide, to prepare a (2S,3S,4S)-1-N-protected-3,4-O-di-protected-5-methylene-2-phthalimido-piperidine-3,4-diol represented by formula (IX):

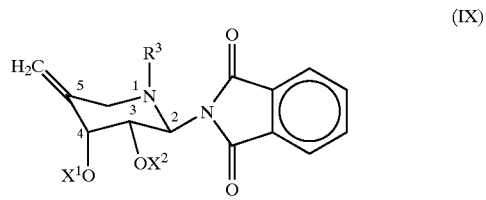

(IX)

wherein $R^3$, $X^1$ and $X^2$ have the same meanings as above;

reducing the double bond at the 5-position of the compound of formula (IX) to convert the methylene group at the 5-position into a methyl group, thereby preparing a (2S,3S,4R,5R)-1-N-protected-3,4-O-di-protected-5-methyl-2-phthalimidopiperidine-3,4-diol represented by formula (X):

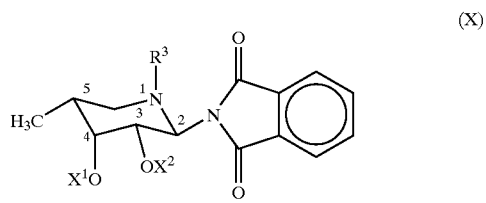

(X)

wherein $R^3$, $X^1$ and $X^2$ have the same meanings as above;

eliminating the phthaloyl group from the 2-amino group of the compound of formula (X) by treatment with hydrazine or an acid, to prepare a (2R,3S,4R,5R)-2-amino-1-N-protected-3,4-O-di-protected-5-methylpiperidine-3,4-diol represented by formula (XI):

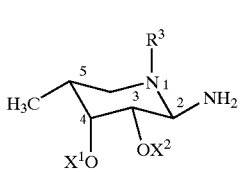

(XI)

wherein $R^3$, $X^1$ and $X^2$ have the same meanings as above;

protecting the amino group at the 2-position of the compound of formula (XI) with a lower alkanoyl group or a lower ω-trihaloalkanoyl group ($R^2$), to prepare a compound represented by formula (XII):

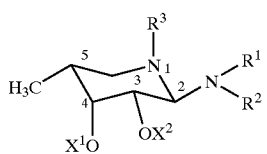

(XII)

wherein $R^3$, $X^1$ and $X^2$ have the same meanings as above, $R^1$ is a hydrogen atom and $R^2$ is a lower alkanoyl group or a lower ω-trihaloalkanoyl group; and then eliminating both the imino-protecting group ($R^3$) and the hydroxyl-protecting groups ($X^1$ and $X^2$) of the compound of formula (XII), or alternatively eliminating the imino-protecting group and the hydroxyl-protecting groups ($X^1$ and $X^2$) immediately from the compound of formula (X) or (XI), to give the compound of the formula (I).

* * * * *

UNITED STATES PATENT AND TRADEMARK OFFICE
CERTIFICATE OF CORRECTION

PATENT NO.     : 6,610,709 B1
DATED          : August 26, 2003
INVENTOR(S)    : Nishimura et al.

It is certified that error appears in the above-identified patent and that said Letters Patent is hereby corrected as shown below:

<u>Title page,</u>
Item [87], should read:
-- [87]   PCT Pub. No.   WO00/49200
           PCT Pub. Date: August 10, 2000 --

Signed and Sealed this

Ninth Day of December, 2003

JAMES E. ROGAN
*Director of the United States Patent and Trademark Office*